United States Patent
Zavilenski et al.

(10) Patent No.: US 6,371,760 B1
(45) Date of Patent: Apr. 16, 2002

(54) METHOD AND APPARATUS FOR WELDING ORTHODONTIC ARTICLE AND AN ORTHODONTIC ARTICLE

(75) Inventors: Tony Zavilenski, 427 Trailblaze Pass, Murrieta, CA (US) 92562; Max Eagleson, Rte.2, Box 185, Keota, OK (US) 74941; Ron Hagen, 235 E. Santa Clara #305, San Jose, CA (US) 95113; Yongjin Xie, 7941 October Way; Richard Sam, 10811 Barrington Bridge Ct., both of Cupertino, CA (US) 94014

(73) Assignees: Tony Zavilenski; Max Eagleson; Ron Hagen; Yongjin Xie; Richard Sam, all of Santa Clara, CA (US)

( * ) Notice: Subject to any disclaimer, the term of this patent is extended or adjusted under 35 U.S.C. 154(b) by 0 days.

(21) Appl. No.: 09/470,142

(22) Filed: Dec. 22, 1999

(51) Int. Cl.[7] .................................................. A61C 3/00
(52) U.S. Cl. .............................................. 433/8; 433/9
(58) Field of Search ........................... 433/9, 8, 10, 11, 433/12

(56) References Cited

U.S. PATENT DOCUMENTS

| | | | |
|---|---|---|---|
| 4,249,060 A | 2/1981 | Colby | 433/24 |
| 4,256,455 A | 3/1981 | Förster | 433/8 |
| 4,386,909 A | 6/1983 | Hanson | 433/20 |
| 4,482,318 A | 11/1984 | Förster | 433/7 |
| 4,627,816 A * | 12/1986 | Gunzel | 433/11 |
| 4,752,221 A | 6/1988 | Hanson et al. | 433/9 |
| 4,842,513 A | 6/1989 | Haarmann | 433/9 |
| 5,111,277 A * | 5/1992 | Medeiros, III et al. | 357/74 |
| 5,337,033 A | 8/1994 | Kinoushi et al. | 433/189 |
| RE35,170 E | 3/1996 | Arndt et al. | 433/7 |
| 5,692,898 A | 12/1997 | Orikasa et al. | 433/8 |
| 5,711,665 A | 1/1998 | Adam et al. | 433/9 |
| 5,711,666 A | 1/1998 | Hanson | 433/11 |
| 5,746,593 A | 5/1998 | Förster | 433/8 |
| 5,753,884 A | 5/1998 | Hilgenfeldt et al. | 433/8 |
| 5,779,477 A | 7/1998 | Boss | 433/172 |
| 5,813,854 A | 9/1998 | Nikoden | 433/29 |
| 5,871,350 A | 2/1999 | Clark et al. | 433/18 |

* cited by examiner

Primary Examiner—John J. Wilson
(74) Attorney, Agent, or Firm—Douglas A Chaikin; Peninsula IP Group

(57) ABSTRACT

Disclosed herein is an orthodontic article, a method of making an orthodontic article and an apparatus for making the orthodontic article. The orthodontic article is made by laser welding the work piece, comprising a bracket body and a the pad, together. The article thus formed includes a laser-welded seal around the perimeter of the adjoining areas between the pad and the bracket body. In an exemplary embodiment the apparatus of the invention, makes a series of closely spaced spot welds. The spot welds, in an exemplary embodiment, are significantly overlapped that they form a seal around the entire perimeter of the work piece adjoining areas. The spot welds, in an exemplary embodiment, are significantly overlapped that they form a hermetic seal between the pad and the bracket body. In other exemplary embodiments, the process of manufacturing orthodontic articles is automated and controlled by a computer and computer software.

6 Claims, 12 Drawing Sheets

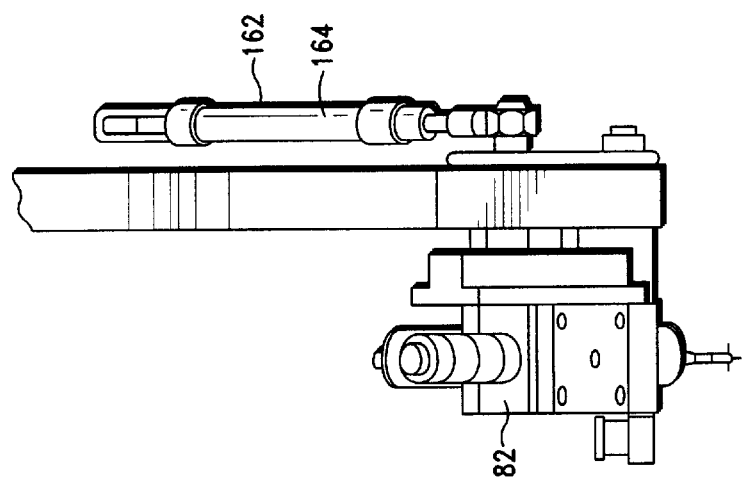
FIG.-16
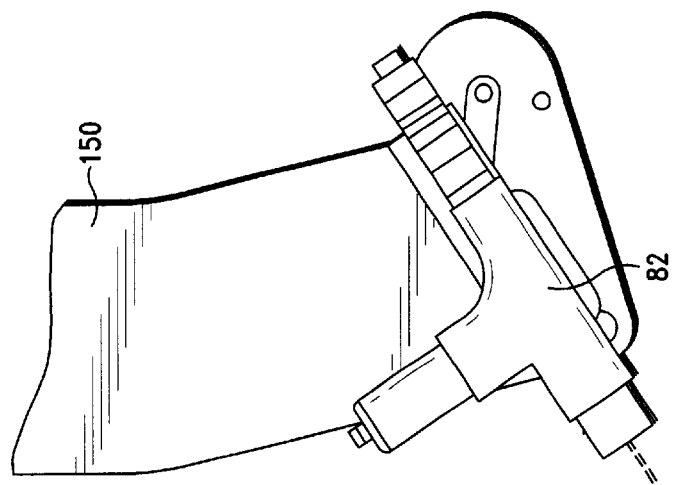
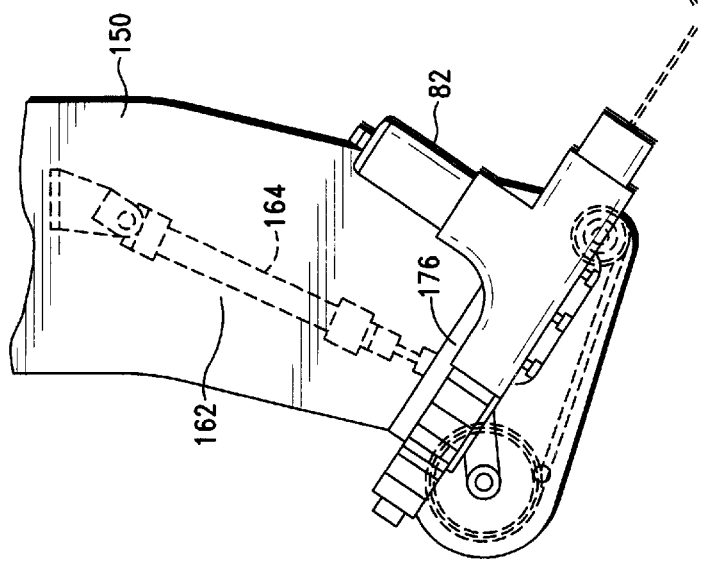
FIG.-15

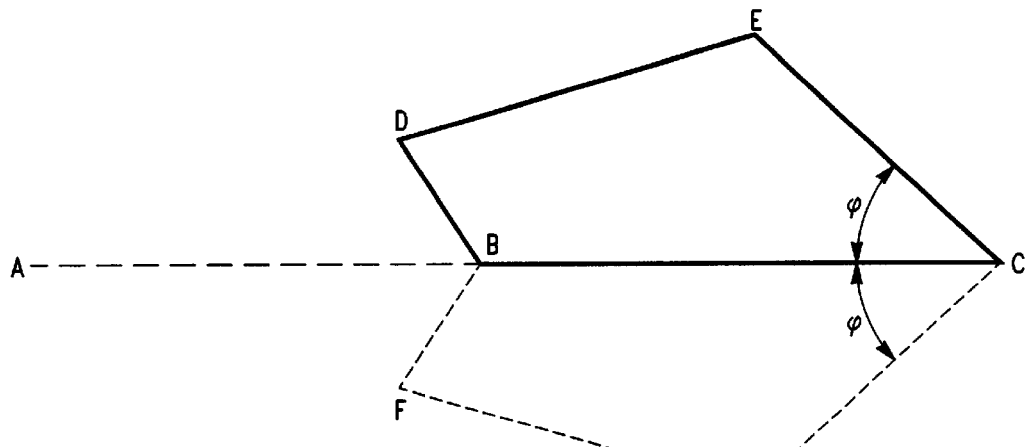
FIG.—18
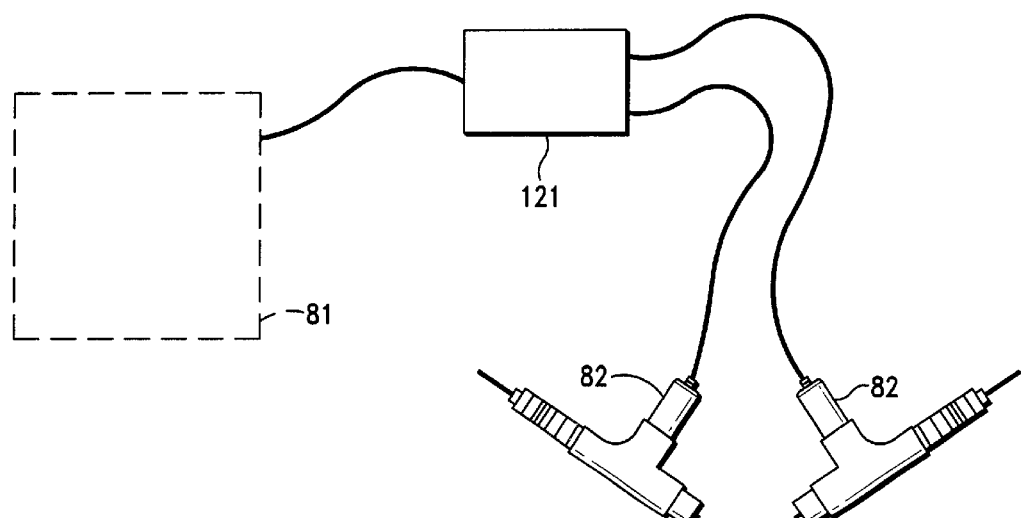
FIG.—27

METHOD AND APPARATUS FOR WELDING ORTHODONTIC ARTICLE AND AN ORTHODONTIC ARTICLE

BACKGROUND OF THE INVENTION

1. Field of the Invention

This invention relates generally to the welding of orthodontic articles and in particular, the method, apparatus and the orthodontic article itself. In particular, this invention relates to a method of laser welding the orthodontic article and the apparatus for accomplishing the method by an automated process.

2. Background

An orthodontic device known commonly as braces comprises two elements, namely, a bracket body and a pad. The elements are typically made separately and then permanently connected to one another for use. In some cases, the bracket body is tack welded to the pad, which is fabricated in strip form to facilities an automated permanent binding of the bracket body to the pad.

The pad is sized and shaped to conform to the teeth of the user and the surface contacting the teeth is generally concave. Adhesive is applied to the concave surface of the pad for facilitating a bond between the orthodontic device and the teeth of the user.

The bracket body provides the guiding structure for the arch wire and provides tie wings for manipulation for aligning and adjusting of the fit between the teeth and the brace. The arch wire goes around the braces and supports and aligns the teeth according to the expert manipulations of the dentist.

Typically, the bracket body is tack welded or otherwise only semi-permanently adhered to the pad. A gold braise or weld or similar treatment is then performed to connect the elements of the orthodontic device permanently. However, it is also known that gold braising requires high temperatures which may damage the braise or the elements of the orthodontic device and is not amendable to process automation.

Typical orthodontic devices have been made from materials such as ceramic (U.S. Pat. No. 5,205,734) or metal (U.S. Pat. No. 5,746,593). Some have even tried plastic with metal reinforcement (U.S. Pat. No. 5,692,898). Increasingly some metal material is used in at least part of the orthodontic device. More recently, Titanium is used as one of the elements of the orthodontic device. In fact, many new orthodontic devices are being made where Titanium forms at least a substantial part of the orthodontic device, see the disclosures of U.S. Pat. No. 5,746,593 and U.S. Pat. No. Re. 35,170. Very often some composition of Titanium and Nickel Titanium ($Ni_2Ti_2$) are now being used to form the entire bracket body and the pad.

Unfortunately, conventional methods and techniques for permanently connecting the pad and the bracket are simply ineffective on such Titanium based elements. Additionally, conventional methods of forming the permanent connection between the bracket body and pad are becoming less desirable as the standards for such orthodontic devices becomes more closely regulated. These regulations require that the seal between the pad and the bracket body be complete, in fact, certain state regulations require that the seal between the two elements be hermetic. Neither conventional welding nor gold braising is equipped to create such a seal between the elements. Moreover, neither braising nor conventional welding nor other known techniques can form a proper seal on Titanium based orthodontic products such as those described above.

Other known techniques such as microwelding as described in U.S. Pat. No. 4,249,060 for intra oral welding are similarly ineffective at creating the proper seal described above. Similar methods of making a bracket body of plastic with metal reinforcement (U.S. Pat. No. 5,692,898) are not relevant to the device, method and apparatus of the invention described herein.

In commercial applications, it is desirable to automate the manufacturing process to make the manufacture of such orthodontic devices cost effective. Typically, as illustrated in the drawing herein, the work piece, comprises the pad separated from and needing to be permanently attached to the bracket. The work pieces are provided in the form of strips of tack welded bracket bodies and pads. An automated process and apparatus must be created whereby the work pieces are fed through the joining apparatus to accomplish the permanent bonding. The needed apparatus for accomplishing such permanent bonding must be accurate as the work pieces are quite small and are numerous as well as intricate. Even minor damage or blemishes to the work piece would be sufficient to cause the work piece to be rejected. The rejection of a plurality of work pieces would be catastrophic to the manufacturer's investment. Additionally, the method and apparatus must provide a high quality bond which is impervious to the caustic environment of the human mouth. And, of course, since the work piece is designed to fit within the human body there must be a high degree of quality assurance that each work piece is suited to its purpose.

What is needed is an orthodontic device that fulfills the above requirements made by a method and an apparatus that provide a sustainable return on the manufacturer's investment. This is especially critical when the work piece provided is made from materials such as Titanium or Titanium based alloys. In the disclosed invention, a new, novel and non-obvious method and apparatus is used to create such an orthodontic device.

SUMMARY OF THE INVENTION

It is an object of this invention to provide a orthodontic device, which is laser welded so that the pad is permanently joined to the bracket body by laser welding the two together.

It is an additional object of this invention to provide a method for making such a laser welded device and additionally making a laser welded orthodontic device by an automated process.

It is an additional object of this invention to provide an apparatus for making the laser welded orthodontic device by the method of the invention and for making the laser welded orthodontic device by the automated method of the invention.

In accordance with the above objects and those that will be mentioned and will become apparent below, the orthodontic device in accordance with this invention comprises:

a pad;

a bracket body;

the bracket body being laser welded to the pad.

In an exemplary embodiment, both the pad and bracket body are made from Titanium. Also, in an exemplary embodiment the work piece forms a generally rectangular shape and the pad has one surface with a generally concave shape for the surface which contacts the teeth of the user.

In an exemplary embodiment of the method of the invention, the method of manufacturing which comprises the steps of:

providing a pad and a bracket body;

tack welding the pad and the bracket body together, and laser welding the pad to the bracket body for permanent connection.

In an exemplary embodiment, the method in accordance with the invention includes the step of spot welding at the contacting surfaces between the bracket body and the pad. In an exemplary embodiment, such spot welds are abundant and overlap each other at least partially, so that the perimeter around the work piece, between the bracket body and the pad, forms a seam weld and a seal. In fact, the seal is a hermetic seal between the bracket body and pad and around the perimeter of their joining.

An automated method of providing laser welded orthodontic articles comprises:

providing a strip of work pieces including a pad and a bracket body being tack welded together;

providing a laser member having at least one laser for laser welding together the work pieces;

laser welding at least one side of the work piece; and rotating the laser member to weld a second side of the work piece and continuing rotation of the laser member until the entire perimeter formed by the contacting surfaces of the pad and bracket body are welded.

In another aspect of the invention, an apparatus for manufacturing the orthodontic article, comprises:

a laser welding member for creating a weld on all sides of the work piece;

a laser focusing member for focusing the laser into a single beam;

a laser alignment member for moving the laser welding member around the work piece, for facilitating creating a weld on all sides of the work piece; and an indexer member for moving the work piece into position to be welded.

In an exemplary embodiment the laser welding member includes two laser focusing members spaced approximately 180° apart. The opposed laser members are connected to an overhead rotatable platform, which, after welding, on two sides of the generally rectangular work piece are then rotated to weld the two remaining sides of the work piece.

As noted below in greater detail, the laser focusing members must operate so as not to cause the laser beam to strike either the work piece being welded or an adjacent work piece. In other words, the laser beam must be positioned so as to strike only the desired location. In order to maintain proper yield rates and the desired quality assurance, only that area designated for welding can be struck with a laser beam.

Additionally, in an automated exemplary embodiment, the apparatus in accordance with the invention includes an indexer which includes a mechanism for timing the movement of the next work piece ready for laser welding after the first work piece has been completed.

A computerized exemplary embodiment is also included as part of the invention herein. In this embodiment, the apparatus includes a laser alignment member operated by a computer and computer software. The laser alignment member adjusts and aligns the laser member so that the laser spot welds are positioned precisely in the desired location regardless of the specific configuration of the work piece. It will be appreciated that the work piece may vary in size and shape and the apparatus must be able to easily adapt to such dimensional changes. By providing appropriate software, the dimensional limits of the work piece may be entered into the computer and the computer will make the appropriate adjustments so that the laser alignment member functions as described above. Also, the indexer apparatus and laser focusing members are also controlled by the computer and its software as well as the timing described above.

It is an advantage of this invention to provide a laser welded orthodontic article which includes a hermetic seal around the perimeter of the adjoining surfaces of the pad and the bracket body.

It is an additional advantage of this invention to provide a method of laser welding a series of work pieces to provide economic and well constructed such orthodontic articles, which meet international standards.

It is an additional advantage of this invention to provide an apparatus, which facilitates automated manufacture of orthodontic articles by laser welding.

BRIEF DESCRIPTION OF THE DRAWING

For a further understanding of the objects and advantages of the present invention, reference should be had to the following detailed description, taken in conjunction with the accompanying drawing, in which like parts are given like reference numerals and wherein:

FIGS. 15 and 16 illustrate the opposed laser focusing members connected to the laser aignment member in accordance with this invention.

FIGS. 18 and 19 illustrate, in schematic, the operating principles of the laser alignment member having a four bar linkage in accordance with this invention.

FIG. 27 illustrates in schematic the arrangement of the laser, and the focusing members.

DETAILED DESCRIPTION OF THE INVENTION

While the detailed description of the invention below and the description above are being primarily focused upon orthodontic articles, it will be appreciated that the process and the apparatus for accomplishing that process are not so limited. Particularly, the process and the apparatus for accomplishing that process can be used with non-orthodontic related applications and therefore, neither the process nor the apparatus for accomplishing that process are intended here to be limited to orthodontic applications, devices or appliances. For example, this invention can be extended to any medical device made with stainless steel or titanium alloys, or sensors, which require complicated but reproducible weld schedules.

Figure 1:
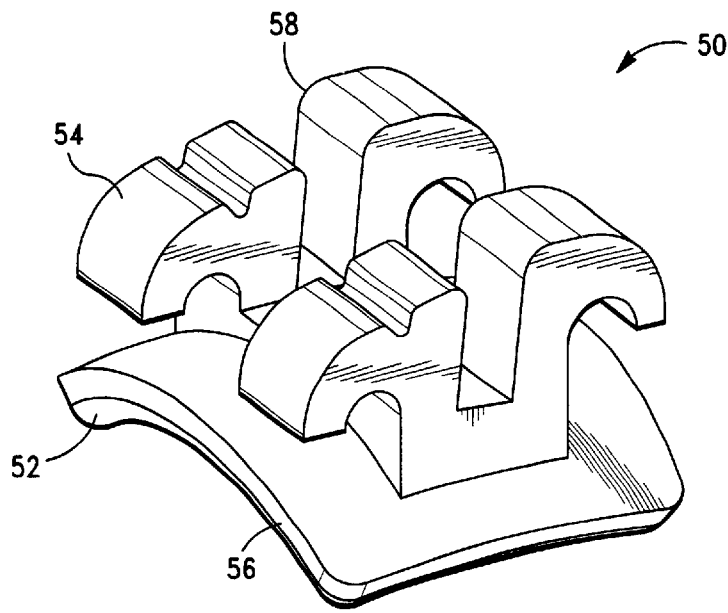
FIG. 1 is a perspective view of an orthodontic device in accordance with this invention.
Figure 20:
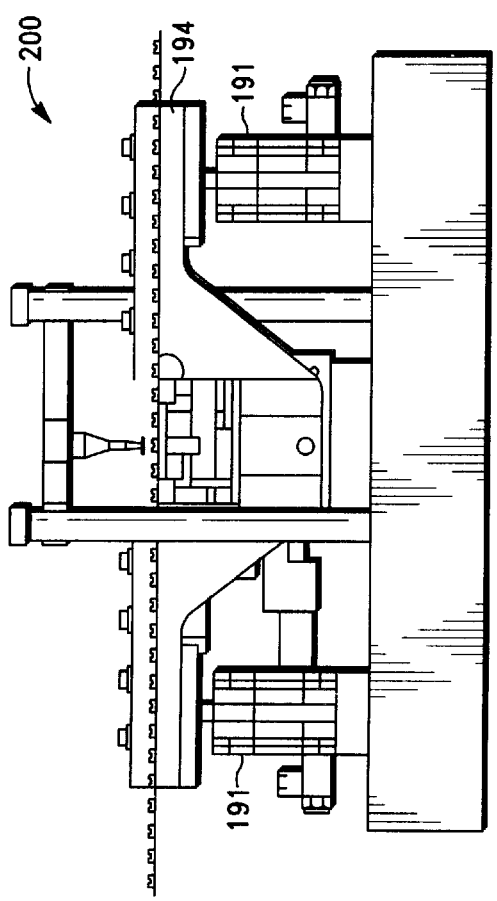
FIGS. 20 through 24 illustrate the indexer assembly in accordance with this invention and the method of operation of the indexer assembly in accordance with the method of this invention.

The invention will now be described with respect to FIG. 1, which illustrates a preferred embodiment of the orthodontic device, shown generally by the numeral 50. The orthodontic device 50 is also known as an orthodontic appliance. The orthodontic device 50 includes a pad 52 and a bracket body 54. The device 50 is tack welded together before laser welding, which means the pad 52 is tack welded to the bracket body 54. In this condition, the device 50 is known as a work piece. Typically, as shown in FIG. 20, the work pieces are strung together on strips waiting laser welding.

The work piece most typically used in this invention is made from Titanium or an alloy of Titanium, such as $Ti_2Ni$. Other materials such as stainless steel or other alloys are also within the scope of this invention. As noted above, conventional welding techniques are ineffective to weld the Titanium work pieces together. An acceptable weld between the pad 52 and bracket body 54 is hermetically sealed and conventional techniques are not capable of accomplishing this result. The hermetic seal prevents food particles, bacteria and the like from becoming lodged in the orthodontic device and thus assists in preventing the spread of bacteria which can cause tooth decay as well as gingivitis.

One side of the pad 52 fits against the teeth while the other side attaches to the bracket body 54. Adhesive is applied between the teeth and the pad 52 for a secure connection to the teeth. The side 56 has a matte finish to facilitate the effectiveness of such adhesive. The pad 52 facilitates such secure connection by being in a concave shape to match the curvature of the teeth.

The bracket body 54 includes longitudinal grove 58 for accommodating a retaining wire. The bracket body 54 also includes tie wings 60 for gripping and manipulating the orthodontic device 50.

Each of the pad 52 and the bracket body 54 have a rectangular shape. As will be more fully appreciated below, the apparatus according to this invention, utilizes this shape in order to make its laser weld. The apparatus for making laser welds in accordance with this invention includes computer software, which can be programmed to move the laser members to perform specific welding tasks.

In order to laser weld the work piece together to form the orthodontic device 50, the work piece and laser must be properly aligned. As will be appreciated with respect to FIGS. 2 and 3, the laser beam must approach the area between the pad 52 and bracket body 54 so that neither the adjacent work piece nor any part of the work piece to be laser welded is contacted by the laser beam. In an exemplary embodiment, the laser beam 62 makes an angle with the horizontal surface upon which the work piece rests as illustrated in FIGS. 2 and 3.

Figure 2:
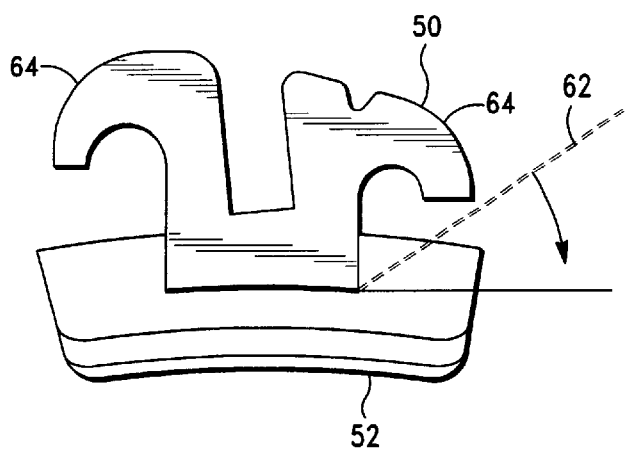
FIG. 2 is a schematic of the orthodontic device in accordance with this invention illustrating weld angles from one side of the orthodontic device.

FIG. 2 illustrates the first welding position where at least one side of the work piece is welded. As seen in FIG. 2, the bracket body 54 has tie wings 60, which form an overhang 64. As the laser beam 62 is focused and aligned on that area of each of the pad 52 and bracket body 54 which contact and mate with one another, defining a mating surface, the laser beam must be careful to miss or avoid completely the overhang 64. Should the laser beam 62 the overhang 64 serious damage to the orthodontic device could result.

Figure 3:
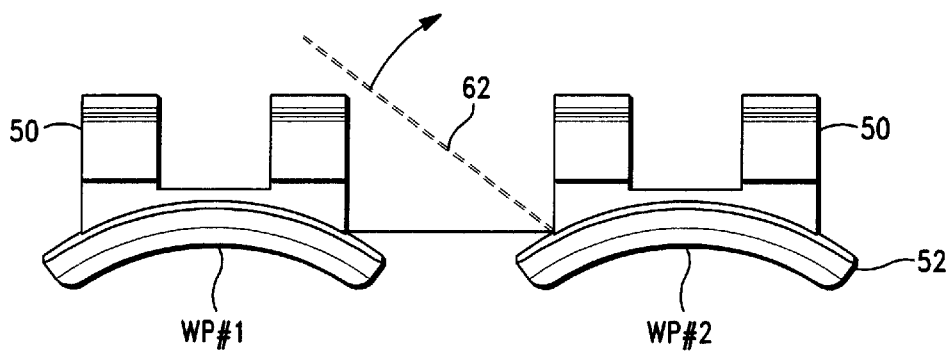
FIG. 3 is a schematic of the orthodontic device in accordance with this invention illustrating weld angles from another side of the orthodontic device.

FIG. 3 illustrates the second welding position, where at least one side of the work piece not previously welded is positioned for welding. In the second position, the laser beam must be carefully focused and aligned so as not to contact any portion of an adjacent work piece. Should the laser beam 62 contact one of the work pieces, serious damage to the adjacent orthodontic device could result.

Since neither of the above conditions are desirable, it is of critical importance to properly focus and align the laser beam 62 to prevent such contact. The only area contacted by the laser beam 62 should be the mating surface defined by the mating contact between the pad 52 and the bracket body 54. At this juncture, the work piece is welded and thus formed into an orthodontic device.

It, as described above, is of critical importance that the weld joint between the pad 52 and the bracket body 54 form a seal, which is hermetic. As explained above health considerations necessitate such a seal.

With respect to FIGS. 12–20, an exemplary apparatus in accordance with this invention is described generally denoted by the numeral 100. The exemplary embodiment 100 includes opposed laser focusing members 82 mounted on a pivotable head, each member is connected to the laser splitter box through an optical fiber. In the first position, the opposed members weld two sides of the work piece. In the second position, the opposed members are rotated 90° as well as re-pivoted and the remaining sides of the work piece are then welded creating a seam weld around the perimeter of the adjoining areas between the pad 52 and the bracket body 54, also known as the mating area. As described herein, this laser weld completely around the perimeter creates seal and in fact, creating a hermetic seal.

In fact, the laser welds around the perimeter of the mating area are not continuous, but rather comprise a series of partially overlapping spot welds. A continuous-wave laser forms a continuous seam as the focus spot is moved during the laser welding process. With a pulsed laser each pulse forms a spot weld at the mating area. The focusing members are moved slightly before the next pulse so that consecutive pulses create overlapping spot welds. As will be appreciated more fully hereinafter, the slight, but very precise movements of the focusing members are controlled by the apparatus' computer controlled servo motor in the computer embodiment of the invention.

In an exemplary embodiment the spot welds overlap 50% or more of the previous weld spot and thus generate a continuous seam weld along the mating area. This leads to a hermetic seal when the entire perimeter has been traversed. It will be noted that this process works equally well with Titanium, its alloys or stainless steel or other metal alloys.

The method of this invention will now be described with respect to FIGS. 4–11. As illustrated, a strip of tack welded work pieces 70 are provided for laser welding. As more clearly illustrated in FIG. 6, the work pieces 70 are provided in strips 72, which may appear in roll form. The work pieces 70 are closely spaced together and provide very little space for focusing a laser beam to weld the perimeter of the mating surfaces as described above.

Figure 4:
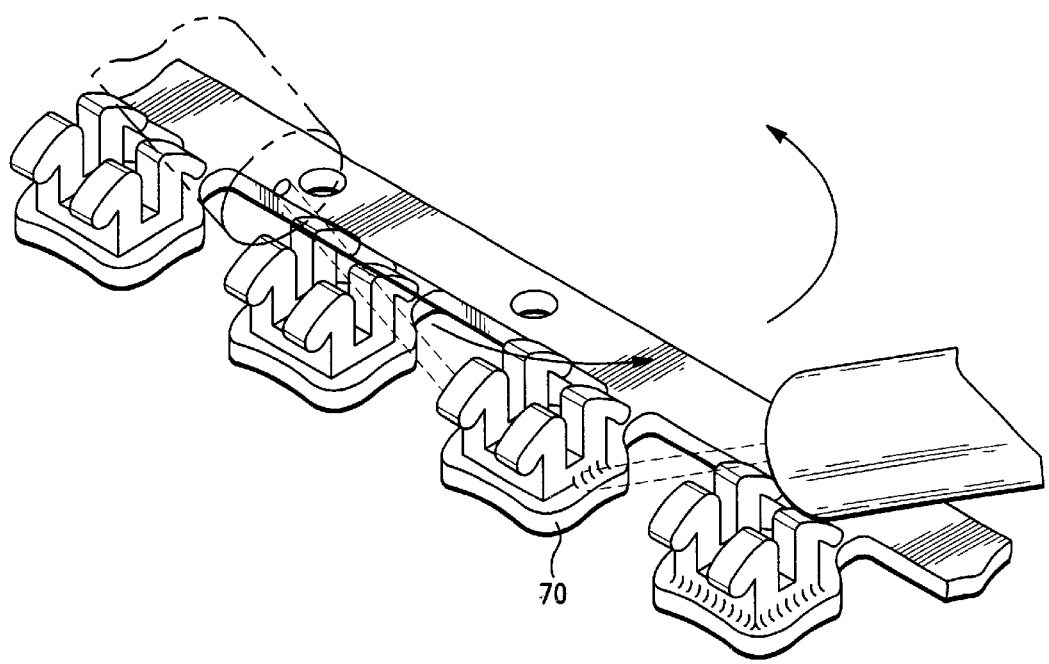
FIG. 4 is an illustration of a strip of orthodontic devices in accordance with the invention being laser welded on one side.
Figure 5:
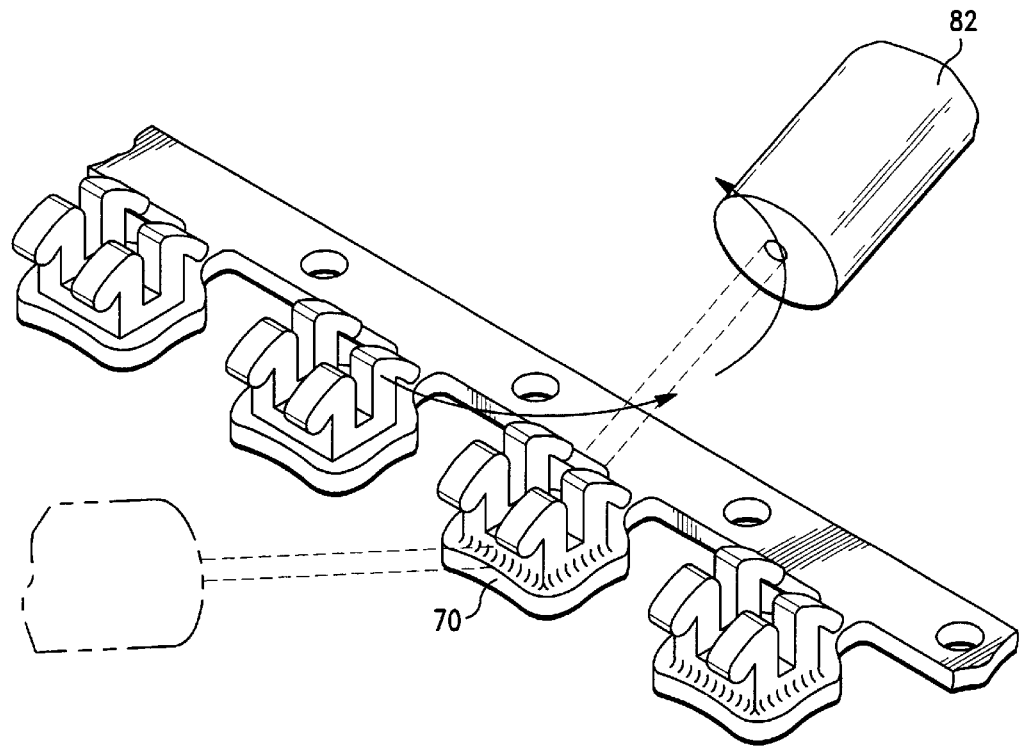
FIG. 5 is an illustration of a strip of orthodontic devices in accordance with the invention being laser welded on the other side.
Figure 6:
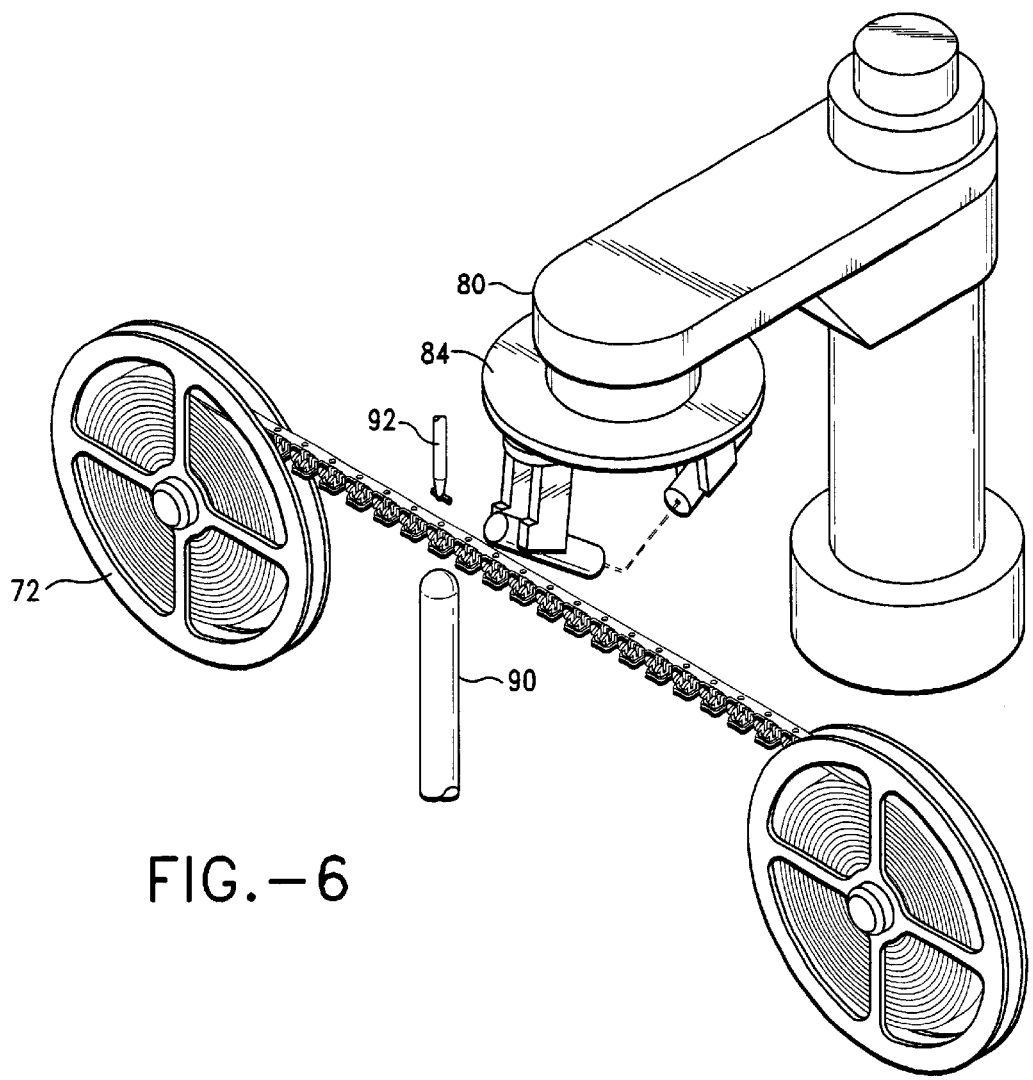
FIG. 6 is an illustration, in schematic, of the automated manufacturing process of a strip of orthodontic devices in accordance with the invention being laser welded on one side.

As particularly illustrated in FIGS. 4–6, a laser focusing assembly 82 includes two opposed focusing members 82 to focus two laser beams for welding two sides of the work piece together as described above, namely, seam welding the pad 52 to the bracket body 54. The laser assembly 80 includes the opposed focusing members 82 suspended on a rotatable table 84.

In the first position, the sides 86 of a work piece 70 are welded. In this first position, the opposed focusing members 82 must be carefully aligned to avoid striking the overhang 64 of each of the work pieces 70. In the second position, the remaining sides of each of the work pieces 70 are welded. In the second position, the members 82 are rotated, preferably 90° and are re-pivoted through the four-bar linkage mechanism to avoid the adjacent work pieces 70 as shown with respect to FIGS. 4–6.

Figures 7, 8:
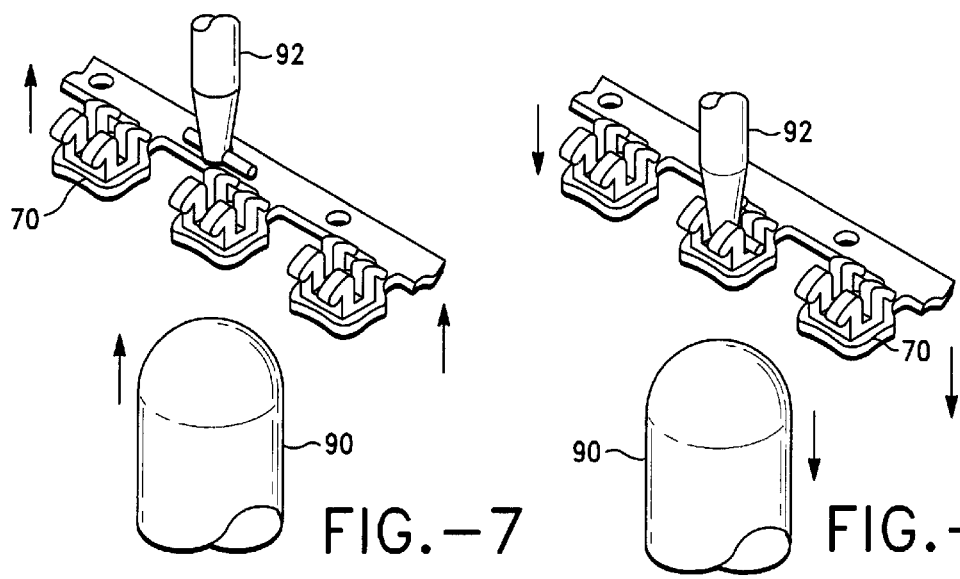
FIGS. 7 and 8 illustrate, in schematic, the orthodontic work piece being loaded before and after laser welding.

As described above, the pad 52 is curved to facilitate adhesion to the teeth. In order to get the best weld possible having the best possible seal and in any case to achieve the hermetic seal, an anvil member 90 is provided to temporarily flatten the pad 52 to provide better mating to the bracket 54. As shown in FIG. 7, an indexing key 92 having a horizontal pin 93 is provided. Although not shown in FIGS. 7 and 8, the apparatus in accordance with this invention provides for structure to raise and lower the strip of work pieces 70 to the key 92.

FIGS. 7 and 8 illustrate, in close up, the steps of applying a temporary pushing and flattening force to the work pieces 70. As noted above, the pad 52 is concave to facilitate adhesion to the teeth. The focusing members 82 are aligned to an optimal location using the key 92 as the reference point to assure proper alignment of the focusing members 82 with the work pieces 70. The focal point is the optimal position for laser welding and occurs when both sides of the work piece 70 can be laser welded without damage to either the equipment or the work piece while producing the intended weldment of orthodontic devices.

The indexing key horizontal pin 93 snugly seats the bracket body 54 upon the raising of the bracket body 54 for connection with the indexing key 92. The indexing key 92 and the horizontal pin 93 are, of course, sized and shaped to match the bracket 54 for a compatible and snug fit. In particular, the horizontal pin 93 is snugly seated in the groove bracket body 54 to provide a snug fit.

Prior to welding, the apparatus moves the work piece 70 into position directly under the indexing key 92. A plunger (FIGS. 20–24) under the anvil member 90 moves the anvil member 90 upward. Raising the strip moves the work piece into seating with the indexing key 92. At the conclusion of the movement of the anvil member 90, the work piece 70 is securely clamped between the indexing key 92 and a temporary flattening force is applied to the work piece 70. The anvil member 90 is sized and shaped to provide such a temporary flattening force as can be appreciated from the drawing.

The apparatus of this invention including at least one laser member 81. Laser welding is commenced with the firing of the pulsed laser members 81.

Upon completion of a particular work piece 70, the work piece 70 and anvil 90 are lowered simultaneously (FIG. 8). Subsequently, and another work piece is moved into position. The next work piece 70 is moved into position by means of a pneumatic actuator which is part of the indexer assembly as described below.

It is an important aspect of the invention that the indexing key 92 be fixed at a specific location as shown in the drawing and as noted above. While the focusing members 82 may be adjusted and moved into position and the alignment members may likewise be moved and adjusted into proper position, the indexing key 92 remains fixed and becomes the focusing and the reference point or positioning guide for all the other members.

It will be noted that using the apparatus of the invention, the optimal position is defined by the location of an indexing key 92. Using the indexing key 92 as the positioning guide allows the apparatus to have a fixed point of reference and provides the accuracy required for obtaining good weld joints.

Figure 9:
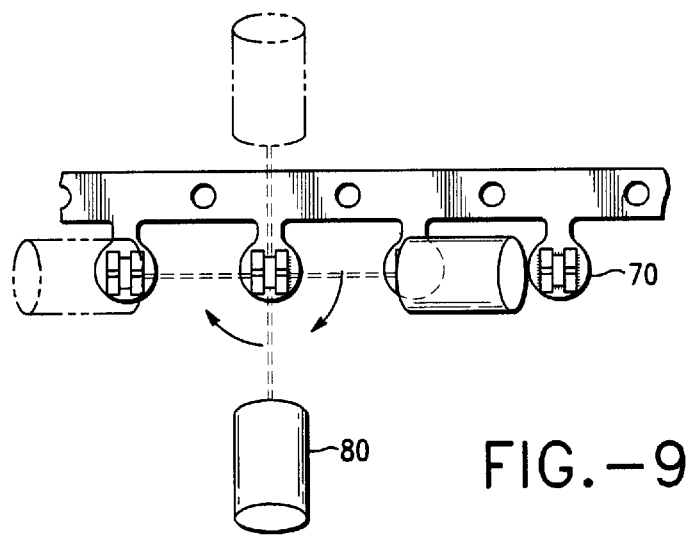
FIG. 9 is an illustration, in schematic, of the orthodontic work piece being laser welded on one side by another exemplary embodiment of the apparatus in accordance with the invention.
Figure 10:
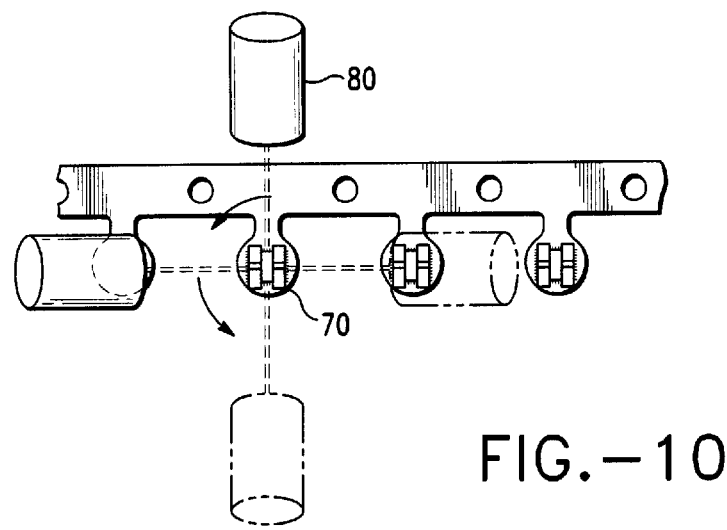
FIG. 10 is an illustration, in schematic, of the orthodontic work piece being laser welded on the other side by the apparatus of FIG. 9.
Figure 11:
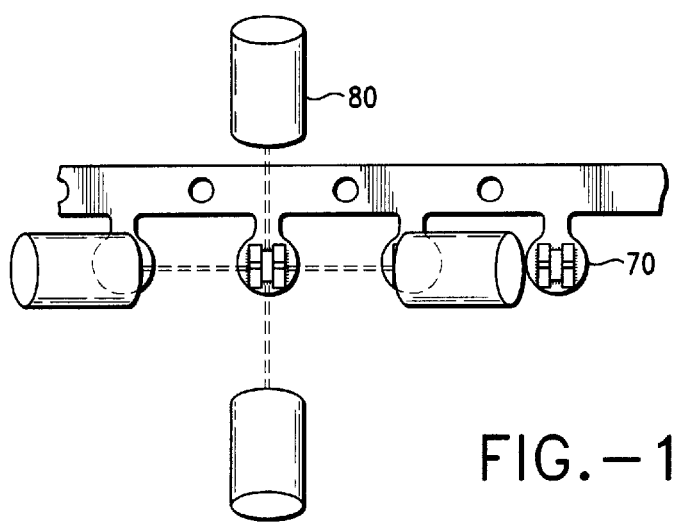
FIG. 11 is an illustration, in schematic, of the orthodontic work piece being laser welded by another exemplary embodiment of the apparatus in accordance with the invention.

With respect to FIGS. 9–11, there is shown two alternative embodiments of the method and apparatus in accordance with this invention. Specifically, with reference to FIGS. 9 and 10, there is shown an orthogonal laser embodiment. In this embodiment, the laser focusing members 82 are orthogonal to one another, instead of being opposed as set forth in FIGS. 1–8 above. As in the first embodiment of the laser focusing members 82, the members 82 are rotated approximately 90° to facilitate completing the seal on all sides of the work piece 70.

With particular reference to FIG. 11, there is shown another embodiment of the laser assembly 80. In this embodiment, there are four laser focusing members 82, which will weld all four sides of the work piece without the necessity of rotation. Of course, it will be appreciated that the alignment and focusing of each of the laser focusing members 82 and laser beams are still required as set forth above.

Figure 13:
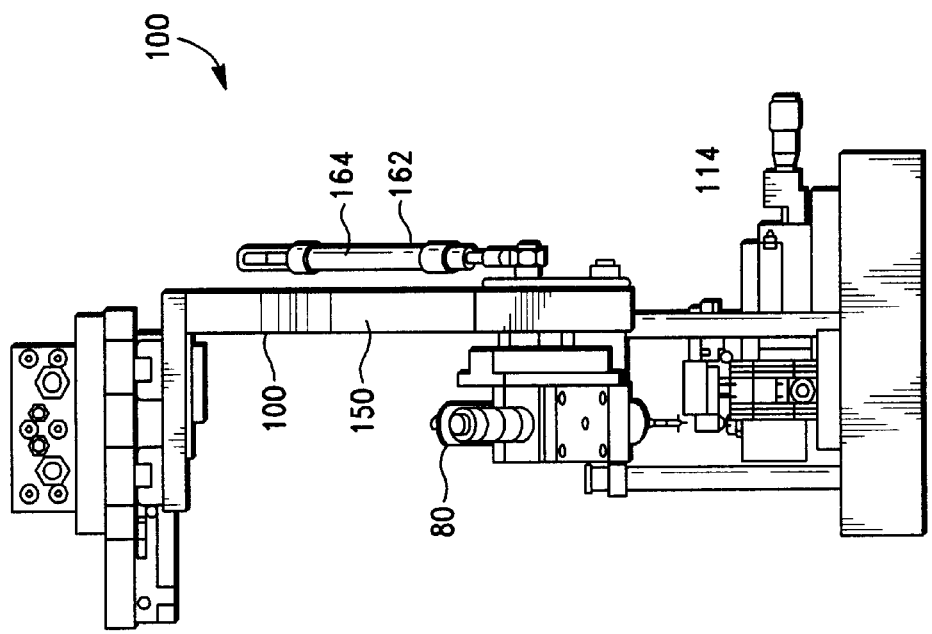
FIG. 13 is an illustration in the orthogonal view of the apparatus in accordance with this invention for manufacturing orthodontic devices illustrating the laser focusing members being opposed and being suspended by the laser alignment member.
Figure 12:
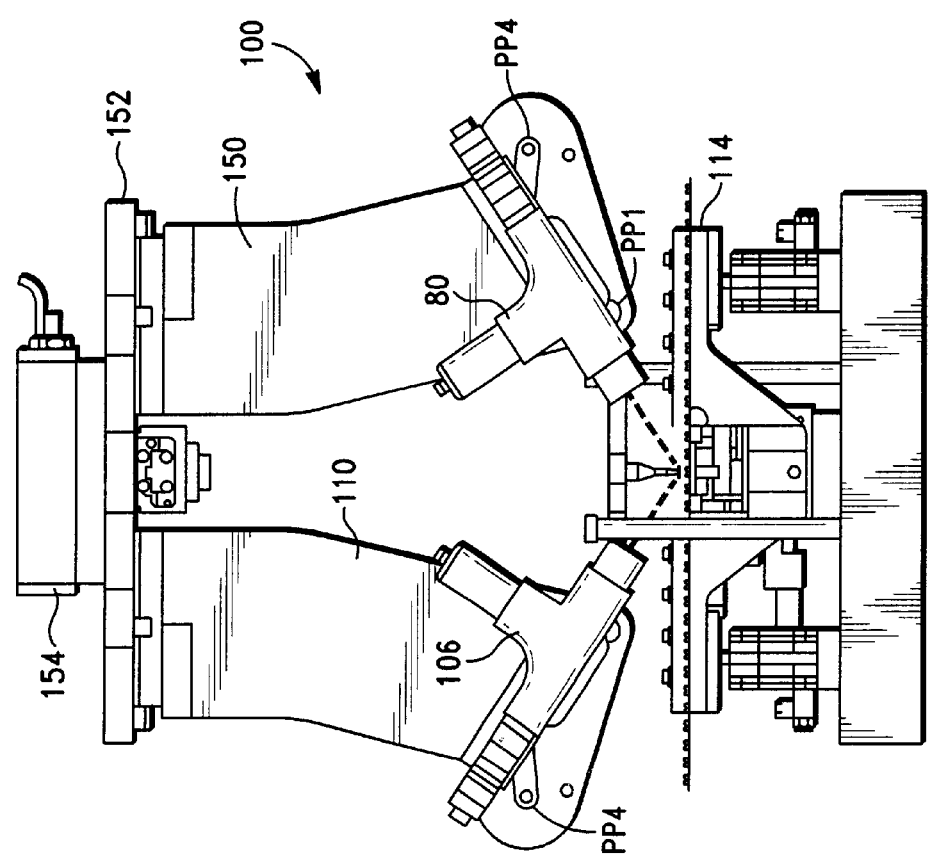
FIG. 12 is a front view of the apparatus in accordance with this invention for manufacturing orthodontic devices illustrating the laser member having opposed lasers suspended by the laser alignment member.

With reference to FIGS. 12–26, and particularly with reference to FIGS. 12 and 13, there is shown an exemplary embodiment of the apparatus in accordance with the invention and generally denoted by the numeral 100. In the exemplary embodiment shown with respect to FIGS. 12 and 13, the apparatus 100 includes, two laser focusing members 82, a laser alignment member 110 and a translation member 114 for moving the work piece 70 into position for welding.

With particular reference to FIG. 27, there is shown the relationship of the laser assembly 80 and the focusing members 82. Power generated by the laser member 81 is delivered by an optical fiber to a beam splitter box 121. The beam splitter box 121 takes the input power divides it into equal proportions, and distribute the equal powers through two optical fibers 119. The optical fibers 119 sends the power to the focusing members 82.

It is well known in the art that output from a laser may be split using beam splitter optics. The output of the laser is divided by divider box 121. In the exemplary embodiment in accordance with this invention, the output of the laser 82 is split in two. Each half is carried by an optical fiber 119. One fiber 119 carries the output to one focusing member 82, the other fiber 119 carries the output of the laser 82 to the opposed focusing member 82.

Figure 14:
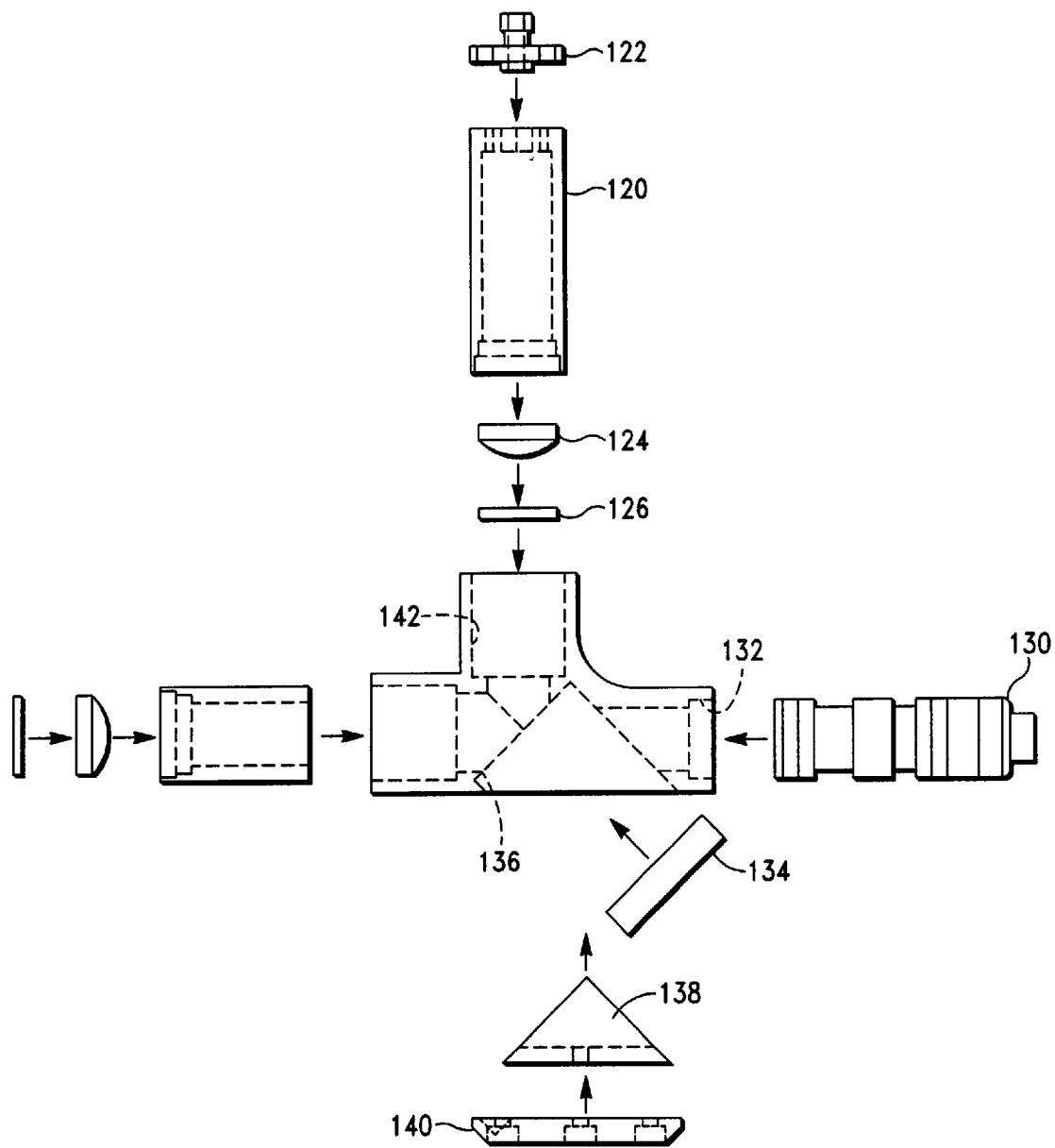
FIG. 14 is an exploded illustration of the laser focusing member in accordance with this invention.

With particular reference to FIG. 14, there is shown an exploded view of the laser focusing member 82. The laser focusing member 82 includes a mating piece 122, beam tube 120, a collimating lens 124, an optics chambers 142, a beam splitter 134, a lens tube 126, an output lens 146, and a CCD Camera 130. The optical fiber 119 is attached to the mating piece 122. The output of the laser 82 is carried by the optical collimating lens 124, which collimates the beam. The collimated beam is then reflected by the beam splitter 134 towards lens 146, while allowing visible light viewing through CCD camera 130.

The lens 146 images the beam to a spot with a spot diameter equal to the diameter of the fiber core times the ratio of the focal lengths of the lenses 124 and 146. The beam splitter 134 reflects near infrared laser light but transmits visible light, thus allowing CCD camera 130 (attached to the focusing cell 142 on the other side of lens 146) to view the area around the focusing spot of lens 146. The camera attached to focusing member 82 assures that the laser beams are in focus and that they are aimed at the correct spot along the mating area.

In order to properly position the focusing member 82, the laser 81 provides an aiming laser. The aiming laser generates an aiming light which co-propagates with the laser beam and serves as a pointer. The CCD camera with attached lens views the aiming light spot on the work pieces 70 and relays the image to a video monitor. The operator views the monitor and adjusts the position of the focusing member 82 until a well focused spot is achieved.

This initializing process is done manually and applies to both focusing members 82. Once, this is done correctly the work pieces 70 are processed. It is a requirement of the preferred method and apparatus of the invention that each of the work pieces be consistent dimensionally. It is also a requirement of the preferred method and apparatus of the invention that the spacing between work pieces 70 also be constant. Once the dimensions and the spacing are known, high efficiency and high yield are easily accomplished by the method and apparatus in accordance with this invention.

With particular respect FIGS. 12–13 and 15–19, there is shown the alignment member 110 in accordance with this invention. The alignment member 110 includes a pair of stanchions 150 extending from a rotary table 152. The rotary table 152 is suspended from an overhanging base 154.

As noted above, the opposed focusing members 82 are connected to the stanchions 150 through an angle adjusting mechanism 160, which is explained in detail with respect to FIGS. 16–19. As clearly seen with respect to FIG. 16, the angle adjusting mechanism 160 includes elevation adjustment mechanism 162. The angle adjusting mechanism 160 provides the opposed focusing members 82 with two orientations for correct alignment during both positions. Namely, the first position wherein the first of the opposed sides of the work piece 70 are welded and the second position wherein the remaining sides of the work piece 70 are welded. The angle adjusting mechanism 160 is pneumatically operated.

The rotary table 152 provides two orientations for each of the focusing members 82 in order to weld the two sides of the work piece 70. In addition, the linkage mechanisms attached to the stanchions 150 provides two different elevation angles for the focusing members 82 to address the work piece 50. First, one side of the work piece 50 is welded and then the linkage mechanism (FIGS. 17–19) moves the focusing members to the other elevation angle. The rotary table 152 is then rotated 90°, and then the laser member 81 is fired to complete the welding operation of the two remaining sides. All of these operations are computer controlled through software.

Figure 17:
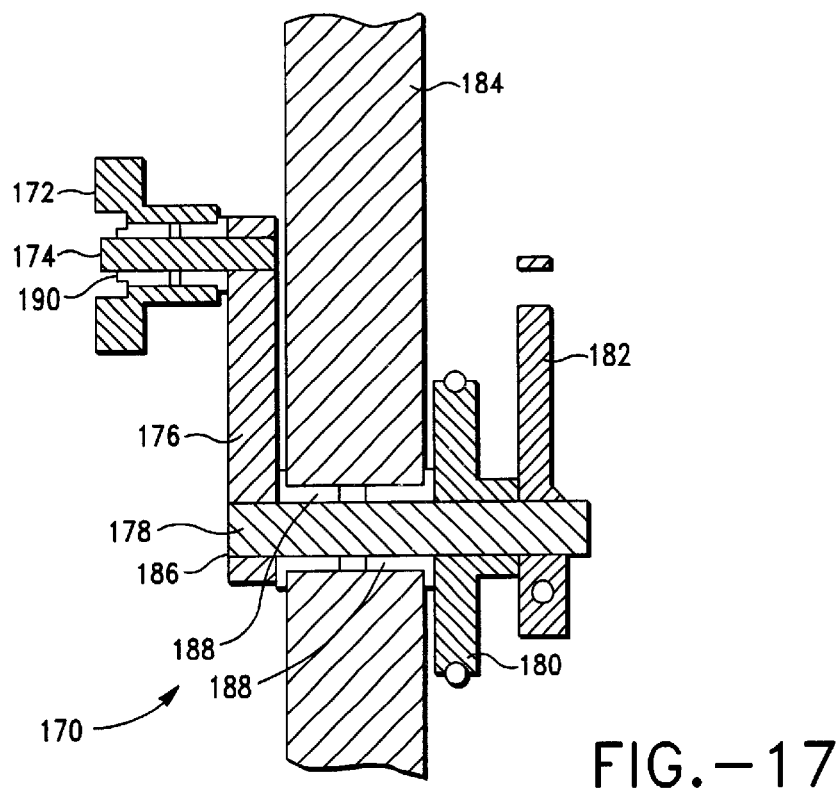
FIG. 17 is a cross sectional view of the laser alignment member having a four bar linkage in accordance with this invention.
Figure 19:
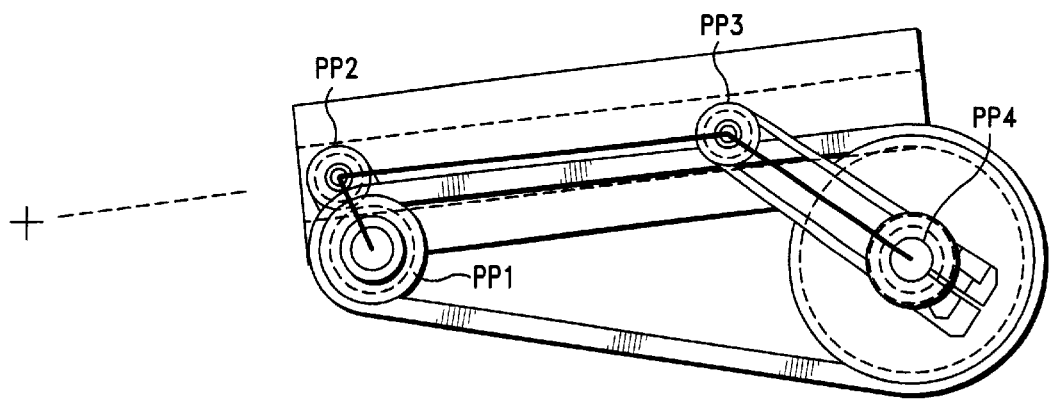

The principle of the four bar linkage is illustrated in FIGS. 17–19. With particular reference to FIG. 18, there is shown the four (4) mechanical bars BC, CE, ED, DB. Each of the bars above are joined at the points C,D,E,B respectively. General geometrical principles provide that if each of the four (4) bars have a start position such that the angle BCE is equal to $\phi$, and only one bar, namely, bar BC is stationary, while the three (3) other bars (CE, ED and DB) are moved, then when the points D and E are moved to positions F and G, respectively, such that the angle BCG is equal to $\phi$, then the distances AD and AF will be the same. For the four (4) bar linkage principle to work, it will be appreciated that the sum BD+BC must be equal to DE+EC.

To utilize the four (4) bar linkage principle in our invention, the focusing member 82 is oriented along the line ED in FIG. 18 so that the focal point of the member 82 is located at A, where ABC is a straight line as shown. The position ED provides the first fixed position for the linkage. The mechanism is devised so that the points D and E can swing past the baseline BC to come to a full stop at positions F and G. At this position, the focusing member 82 is once again focused at position A. A will be the desired position in space for locating the workpiece 70 and that is located at the indexing key 92 as noted above. In this manner, the four (4) bar linkage concept is used to provide the 2 elevation angles for the focusing member.

With particular attention to FIGS. 17 and 19, the four (4) bar linkage as applied to the invention is described. The center points of the parts PP1, PP2, PP3, and PP4 are equivalent to points B, D, E, and C, respectively, in FIG. 18 and definite brackets (FIG. 19). The focusing member 82 is mounted onto the mounting bracket supported by brackets PP2 and PP3. FIG. 17 illustrates, in schematic, the mechanism of adjusting the orientations of the focusing member 82. PP2 and PP3 are ball bearing brackets with a central axle 174. The axle 174 is attached to a beam 176. The movement of the beam 176 is constrained by another axle 178 that is inserted in a ball bearing 188, and the axle 178 in turn drives the movement of pulley 180. The beam 176 is allowed to swing about the axle 178. The pneumatic device 162 is attached on one end to a fixed point on the stanchion 150 (FIG. 15), and the other end of 162 is attached to a point on the beam 176. In the preferred embodiment, the pneumatic device 162 has only two lengths. First, when the air pressure is on, the pneumatic device is extended (long). Second, when the air pressure is off, the pneumatic device is shortened (short). These two positions (long and short) define the two elevation angles of the focusing member. The two pulleys, the centers of which are represented by PP1 and PP4 are connected with a neoprene O-ring belt 192. The purpose of the belt 192 is to ensure that the swing directions of the two beams 176 are the same. In going through a complete 2 swing, the beam BD (FIG. 18) and the beam CE describes different angles. The diameters of the two pulleys PP1 and PP4 are therefore chosen to compensate for this difference in angle described, so that the belt portion attached through PP1 moves the same distance as the belt portion attached through PP4.

The detailed working of the indexer assembly 200 is illustrated with respect to FIGS. 20–24. With particular reference to the figures, there is shown the four (4) pneumatic driven motion elements of the assembly 200 in accordance with the invention which includes, a strip carrier 194, a pair of air cylinders 191, a strip indexer 192, and a plunger cylinder 193.

Figure 21:
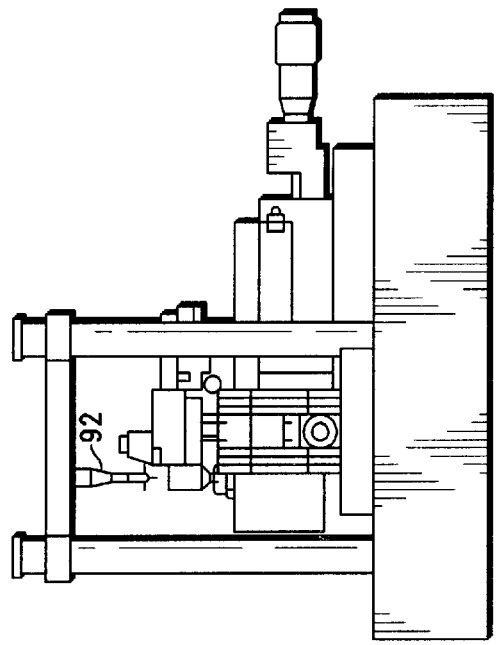
Figure 22:
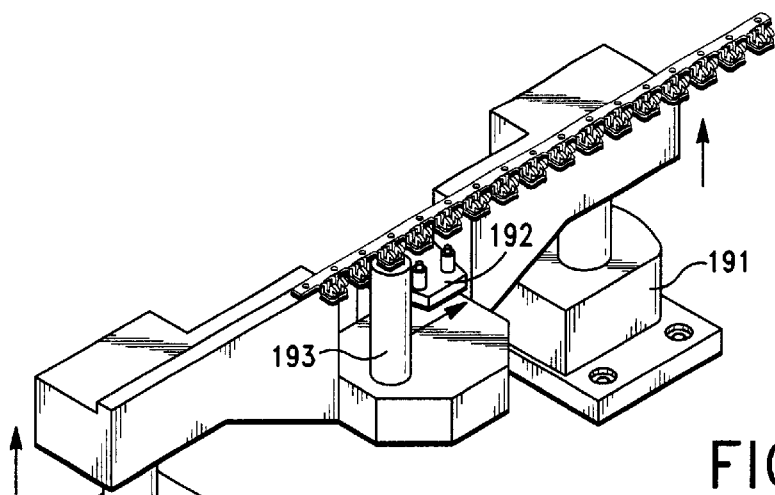
Figure 23:
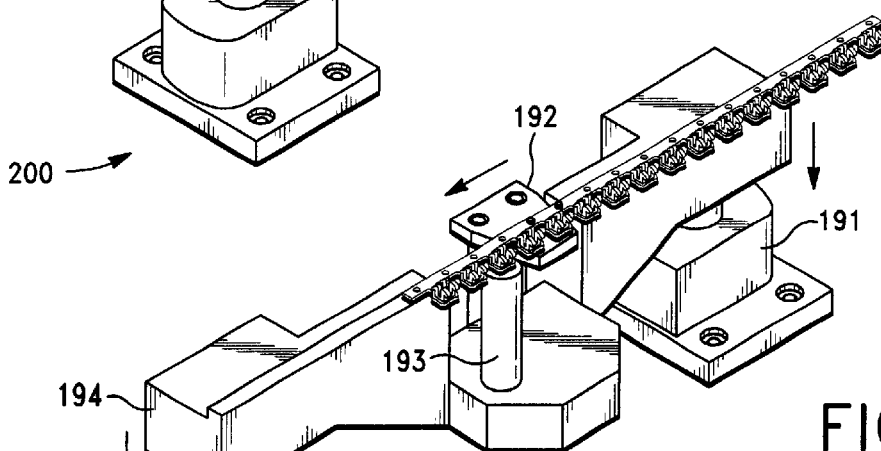
Figure 24:
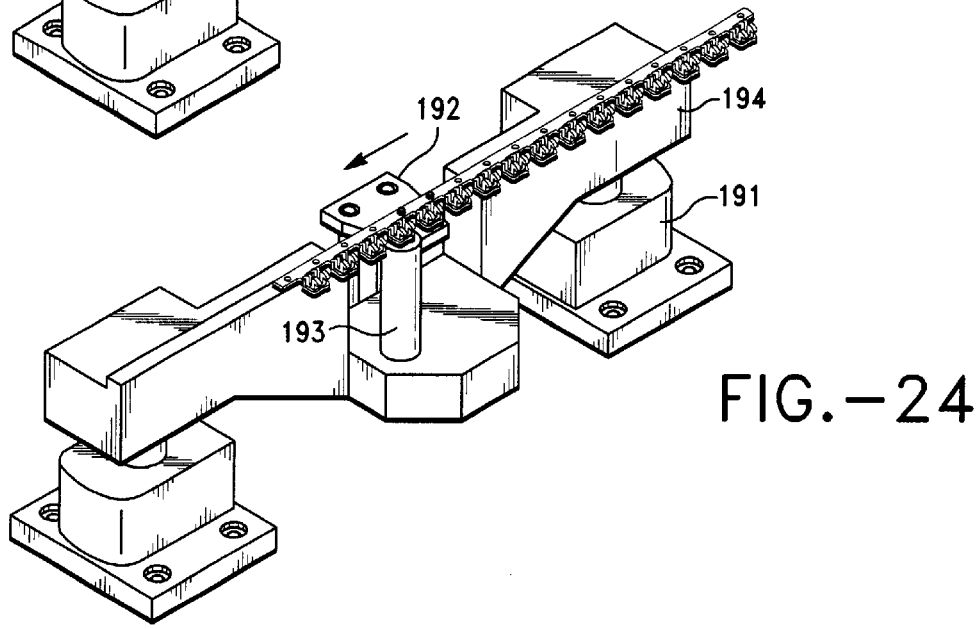
Figure 25:
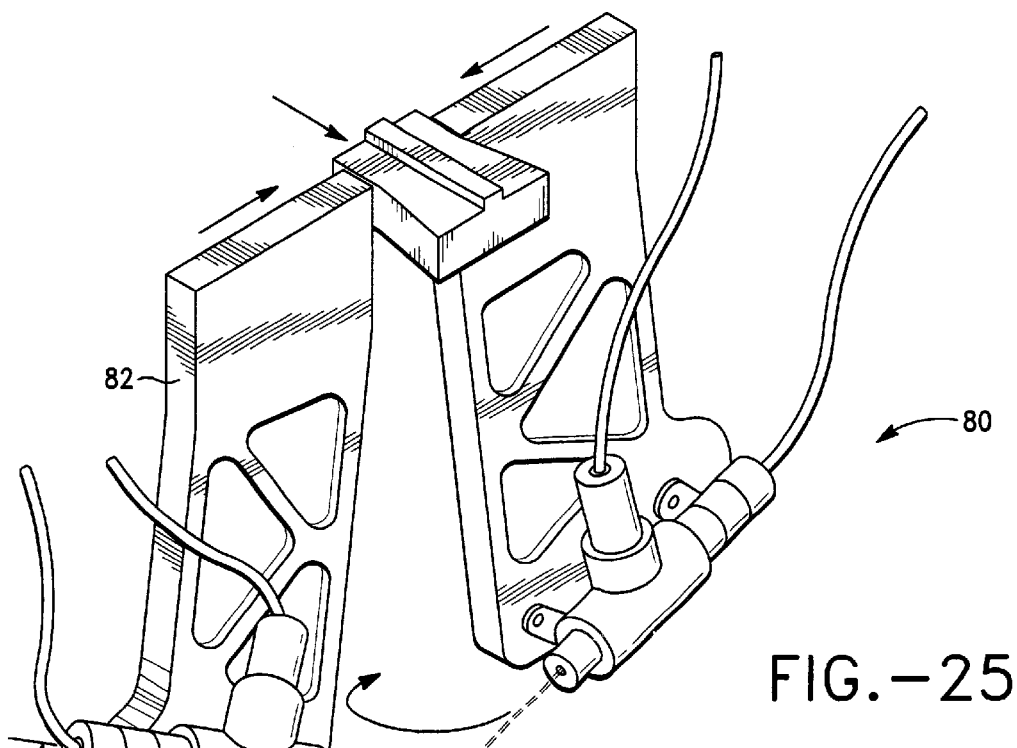
FIGS. 25–26 illustrate, in close up, the opposed focusing members in accordance with this invention in a first and a second position for welding.
Figure 26:
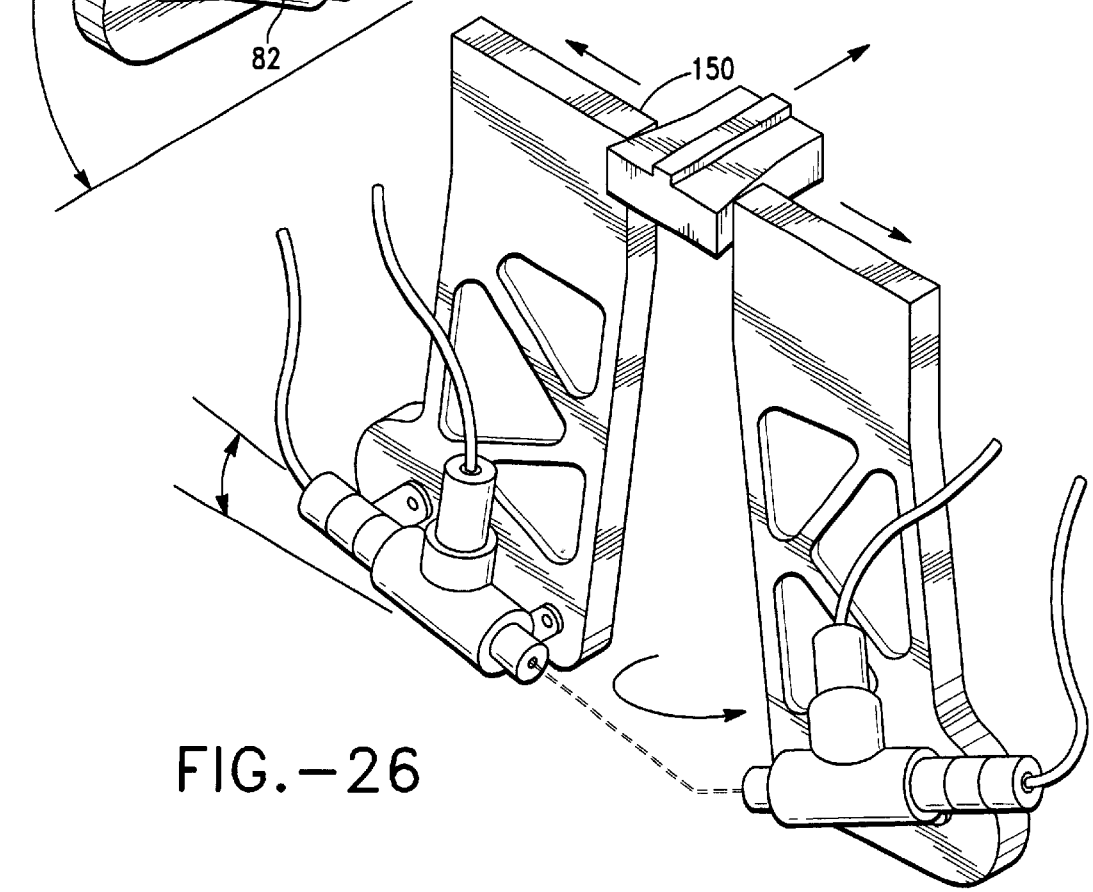

With particular reference to FIGS. 22–24, there is shown the steps of a single weld cycle. FIG. 22 shows a work piece 70 being positioned for welding by the strip indexer 192. As shown, the strip carrier 194 moved upwardly causing the work piece 70 to be brought closer to the indexing key 92 (FIGS. 20 and 21). The upward movement is caused by activating the air cylinders 191. The plunger 193 is then activated and pushes upwardly against the pad 52 to securely seat the work piece 70 in the indexing key 92 (FIG. 7). The indexer 192 continues its independent movement and retreats one step backward to position itself for the next step in alignment with the next work piece 70. The laser then commences to perform welding on work piece 70.

As shown in FIG. 22, upon completion of the welding step, the plunger 193 withdraws, and the air cylinder 191 drops the strip carrier 194 to its low position. The strip indexer 192 includes two 2 pins and these pins engage two new holes on the strip.

As shown in FIG. 24, the indexer 192 advances one step forward for alignment with a new work piece 70. This completes the cycle and a new, unwelded, work piece 70 is now in position for welding. The process repeats itself until the weld of each work piece 70 has been completed.

While the foregoing detailed description has disclosed several embodiments of the orthodontic device, method of manufacturing the orthodontic device and an apparatus for accomplishing both the manufacture of the orthodontic device and carrying out the method of manufacture in accordance with this invention, it is to be understood that the above description is illustrative only and not limiting of the disclosed invention. Particularly, the orthodontic device need not be made from Titanium nor even coated with the same in order to be effective. Also, the apparatus of the invention need not be limited to the exclusive manufacture of orthodontic device. It is believed that the apparatus in accordance with this invention has utility well beyond such orthodontic devices and thus, the claims are not so limited. It will be appreciated that the embodiments discussed above and the virtually infinite embodiments that are not mentioned are easily within the scope and spirit of this invention. Thus, the invention is to be limited only by the claims as set forth below.

What is claimed is:

1. An orthodontic article, comprising:

a pad;

a bracket body;

the pad and the bracket body being made from Titanium; and the bracket body being laser welded to the pad, the laser weld defines a hermetic seal between the bracket body and the pad.

2. The orthodontic article as set forth in claim 1, wherein the pad has a general rectangular shape and additionally forms a concave shape to facilitate attachment of the orthodontic article to the teeth of the user.

3. The orthodontic article as set forth in claim 2, wherein the bracket body has a mating surface with the pad defining a generally rectangular shape, and wherein mating edges are defined along the weld between the bracket body and the pad.

4. The orthodontic article as set forth in claim 3, wherein mating edges of the weld between the pad and the bracket body defines a series of laser spot welds.

5. The orthodontic article as set forth in claim 4, wherein the laser spot welds are significantly overlapped as to define a continuous line.

6. The orthodontic article as set forth in claim 3, wherein the mating area is defined by that area of the pad in mating contact with the bracket body.

* * * * *